US010576218B2

(12) United States Patent
Hasegawa

(10) Patent No.: US 10,576,218 B2
(45) Date of Patent: Mar. 3, 2020

(54) SYRINGE AND INJECTION NEEDLE SAFETY INSTRUMENT

(71) Applicant: NIPRO CORPORATION, Osaka-shi, Osaka (JP)

(72) Inventor: Mitsuru Hasegawa, Osaka (JP)

(73) Assignee: NIPRO CORPORATION, Osaka-Shi (JP)

( * ) Notice: Subject to any disclaimer, the term of this patent is extended or adjusted under 35 U.S.C. 154(b) by 541 days.

(21) Appl. No.: 15/129,322

(22) PCT Filed: Feb. 12, 2015

(86) PCT No.: PCT/JP2015/053768
§ 371 (c)(1),
(2) Date: Sep. 26, 2016

(87) PCT Pub. No.: WO2015/151596
PCT Pub. Date: Oct. 8, 2015

(65) Prior Publication Data
US 2017/0119976 A1  May 4, 2017

(30) Foreign Application Priority Data

Mar. 31, 2014  (JP) ................. 2014-071818

(51) Int. Cl.
*A61M 5/32* (2006.01)
(52) U.S. Cl.
CPC .......... *A61M 5/3275* (2013.01); *A61M 5/321* (2013.01); *A61M 5/3243* (2013.01); *A61M 5/3257* (2013.01)
(58) Field of Classification Search
CPC .. A61M 5/3275; A61M 5/321; A61M 5/3243; A61M 5/3257
See application file for complete search history.

(56) References Cited

U.S. PATENT DOCUMENTS 4,883,469 A * 11/1989 Glazier ............... A61M 5/3216
604/192
5,151,089 A * 9/1992 Kirk, III ............. A61M 5/3216
604/192
(Continued)

FOREIGN PATENT DOCUMENTS

EP    0887082 A2   12/1998
JP    9-103487 A    4/1997
(Continued)

OTHER PUBLICATIONS

Extended European Search Report issued in European Application No. 15772842.9 dated Sep. 18, 2017.

*Primary Examiner* — Amber R Stiles
*Assistant Examiner* — John A Doubrava
(74) *Attorney, Agent, or Firm* — Birch, Stewart, Kolasch & Birch, LLP

(57) ABSTRACT

A syringe includes a barrel, a plunger, an injection needle, and an injection needle safety instrument. The injection needle safety instrument has a base portion fixed to the barrel, a cover portion which can cover a pointed end of a needle tube of the injection needle, and a hinge portion which pivotably couples the base portion and the cover portion. The cover portion is constructed to be pivotable between a first position at which the cover portion is held to the base portion as a first locked portion is locked by a locking portion of the base portion and a second position at which the cover portion covers the pointed end of the needle tube and is held to the injection needle as a second locked portion is locked to the same. The cover portion is tilted toward the barrel in the first position.

20 Claims, 8 Drawing Sheets

(56) References Cited

U.S. PATENT DOCUMENTS

| | | | |
|---|---|---|---|
| 5,599,318 | A | 2/1997 | Sweeney et al. |
| 5,746,726 | A | 5/1998 | Sweeney et al. |
| 2003/0036732 | A1 | 2/2003 | Marano-Ford |
| 2003/0191438 | A1 | 10/2003 | Ferguson et al. |
| 2005/0049560 | A1 | 3/2005 | Hauri |
| 2005/0065481 | A1 | 3/2005 | Hauri et al. |
| 2008/0208138 | A1 | 8/2008 | Lim et al. |
| 2010/0198152 | A1* | 8/2010 | Haindl ............ A61M 5/3216 604/110 |
| 2016/0296712 | A1* | 10/2016 | Minix ............ A61M 5/3216 |

FOREIGN PATENT DOCUMENTS

| | | |
|---|---|---|
| JP | 10-94606 A | 4/1998 |
| JP | 11-57005 A | 3/1999 |
| JP | 2003-220139 A | 8/2003 |
| JP | 2004-538099 A | 12/2004 |
| JP | 2005-521537 A | 7/2005 |
| JP | 2007-503871 A | 3/2007 |
| WO | WO 03/011356 A2 | 2/2003 |
| WO | WO 2008/076459 A1 | 6/2008 |
| WO | WO 2009/007718 A1 | 1/2009 |

\* cited by examiner

SYRINGE AND INJECTION NEEDLE SAFETY INSTRUMENT

TECHNICAL FIELD

The present invention relates to an injection needle safety instrument used as being assembled to a barrel of a syringe and to a syringe including the same.

BACKGROUND ART

Variously constructed injection needle safety instruments have conventionally been proposed in order to prevent inadvertent sticking of an injection needle into a finger or the like.

For example, Japanese Patent Laying-Open No. 11-57005 (PTD 1) discloses an injection needle safety instrument consisting of a single member constructed to safely be removable from a barrel without sticking of an injection needle into a finger or the like after a syringe is used.

The injection needle safety instrument disclosed in Japanese Patent Laying-Open No. 11-57005 includes a hub and a shield pivotably coupled to each other with a hinge being interposed. After a syringe is used, the hub is fixed to a needle tube of an injection needle constituted of the needle tube and a needle hub, the shield is fixed to the hub by pivoting the shield while the shield covers a pointed end of the needle tube, and the injection needle together with the injection needle safety instrument is removed from the barrel by applying external force to the injection needle safety instrument in this state in a direction across an axial line of the barrel.

Japanese National Patent Publication No. 2007-503871 (PTD 2) discloses an injection needle safety instrument consisting of a single member assembled in advance to an injection needle such that the injection needle does not stick into a finger or the like after a syringe is used.

The injection needle safety instrument disclosed in Japanese National Patent Publication No. 2007-503871 includes a collar and a protection housing pivotably coupled to each other with a hinge being interposed, the collar is fixed in advance to a needle hub of an injection needle constituted of a needle tube and the needle hub, and the protection housing can be fixed to the collar by pivoting the protection housing after the syringe is used, while a pointed end of the needle tube is covered with the protection housing.

Japanese National Patent Publication No. 2005-521537 (PTD 3) discloses various injection needle safety instruments each constituted of a plurality of members assembled in advance to a barrel such that an injection needle does not stick into a finger or the like after a syringe is used.

Many of the various injection needle safety instruments disclosed in Japanese National Patent Publication No. 2005-521537 each include a hub attached to a barrel as well as a manual operation portion and a shield which are coupled to the hub with various links being interposed, and the shield can be fixed to the manual operation portion or the link by pivoting the shield by operating the manual operation portion after the syringe is used, while a pointed end of a needle tube is covered with the shield.

CITATION LIST

Patent Document

PTD 1: Japanese Patent Laying-Open No. 11-57005
PTD 2: Japanese National Patent Publication No. 2007-503871
PTD 3: Japanese National Patent Publication No. 2005-521537

SUMMARY OF INVENTION

Technical Problem

The injection needle safety instrument disclosed in Japanese Patent Laying-Open No. 11-57005 is premised on attachment thereof to a syringe after the syringe is used and assembly thereof to the syringe in advance is not assumed. In this connection, the injection needle safety instruments disclosed in Japanese National Patent Publications Nos. 2007-503871 and 2005-521537 assume assembly thereof in advance to a syringe and they are highly convenient in that the injection needle safety instrument does not have to be attached again to a syringe after use.

In the injection needle safety instrument disclosed in Japanese National Patent Publication No. 2007-503871, however, the protection housing is fixed only while the pointed end of the needle tube is covered with the protection housing. While the pointed end of the needle tube is not covered with the protection housing, the protection housing can freely move. Therefore, the protection housing causes interference during injection and handleability during injection is disadvantageous.

In the injection needle safety instrument disclosed in Japanese National Patent Publication No. 2005-521537, the shield is held by another portion of the injection needle safety instrument while the pointed end of the needle tube is not covered with the shield. Therefore, in this regard, this injection needle safety instrument can be concluded to be better in handleability than the injection needle safety instrument disclosed in Japanese National Patent Publication No. 2007-503871. The injection needle safety instrument disclosed in Japanese National Patent Publication No. 2005-521537, however, has a complicated structure, and therefore it is not only high in cost but also significantly cuts off a view of a doctor or the like who handles the syringe at the time of injection because the manual operation portion or the shield considerably protrudes outward from an outer circumferential surface of the syringe while the pointed end of the needle tube is not covered with the shield. The injection needle safety instrument is thus highly disadvantageous in operability during injection.

Therefore, the present invention was made to solve the problems described above, and an object of the present invention is to provide an injection needle safety instrument which has a simplified construction and does not cause interference during injection and a syringe including the same.

Solution to Problem

A syringe based on the present invention includes a barrel, an injection needle attached to a front end portion of the barrel, a plunger attached to the barrel by being inserted into the barrel from a side of a rear end portion of the barrel, and an injection needle safety instrument assembled to the barrel. The injection needle safety instrument includes a base portion including a fixed portion fixed to the barrel, a cover portion including an accommodation portion which can cover a pointed end of a needle tube included in the injection needle by accommodating the pointed end of the needle tube, and a hinge portion which pivotably couples the base portion and the cover portion to each other. The hinge portion has a pivot axis extending in a direction orthogonal to an axial line of the barrel. The base portion is provided with a locking portion and the cover portion is provided with a first locked portion locked to the locking portion and a second locked portion locked to the injection needle. The cover portion is constructed to be pivotable between a first position at which the pointed end of the needle tube is exposed as the cover portion is arranged on the side of the rear end portion of the barrel relative to the pivot axis of the hinge portion along a direction of the axial line of the barrel and the cover portion is held to the base portion as the locking portion locks the first locked portion and a second position at which the cover portion covers the pointed end of the needle tube as the cover portion is arranged on a side of the pointed end of the needle tube relative to the pivot axis of the hinge portion along the direction of the axial line of the barrel and the cover portion is held to the injection needle as the injection needle locks the second locked portion. The cover portion is located as being tilted such that the cover portion comes closer to the barrel from a side of a base end which is a side where the hinge portion is located toward a tip end which is a side where the hinge portion is not located while the cover portion is arranged in the first position and is arranged in the second position as the cover portion pivots by an angle beyond 180° around the pivot axis of the hinge portion.

In the syringe based on the present invention, preferably, an outer geometry of a portion of the cover portion located on the side of the hinge portion is in such a tilted shape as being closer to the barrel in a direction toward the pointed end of the needle tube along the direction of the axial line of the barrel while the cover portion is arranged in the first position.

In the syringe based on the present invention, preferably, the pivot axis of the hinge portion is provided on the side of the pointed end of the needle tube relative to the fixed portion in the direction of the axial line of the barrel.

In the syringe based on the present invention, preferably, the pivot axis of the hinge portion is provided on an outer side of the base portion in a radial direction of the barrel.

In the syringe based on the present invention, preferably, the locking portion is provided on the side of the rear end portion of the barrel relative to the fixed portion in the direction of the axial line of the barrel.

In the syringe based on the present invention, preferably, the second locked portion is in a shape of a hook by which the needle tube can be caught.

In the syringe based on the present invention, preferably, the injection needle safety instrument is formed from an injection molded product consisting of a single member made of a resin, and in that case, preferably, the pivot axis of the hinge portion is formed from a small-thickness portion of which thickness is formed to be smaller than a portion around the small-thickness portion.

In the syringe based on the present invention, the barrel may include a cylindrical body to which the plunger is attached and an adapter which is attached as being externally attached around a front end of the cylindrical body and to which the injection needle is attached. In that case, preferably, the injection needle safety instrument is assembled to the adapter in a portion externally attached around the cylindrical body.

In the syringe based on the present invention, the barrel may be filled with a medicament as being externally hermetically sealed.

An injection needle safety instrument based on the present invention is used as being assembled to a barrel of a syringe, and the injection needle safety instrument includes a base portion including a fixed portion fixed to the barrel of the syringe, a cover portion including an accommodation portion which can cover a pointed end of a needle tube included in an injection needle by accommodating the pointed end of the needle tube attached to a front end portion of the syringe, and a hinge portion which pivotably couples the base portion and the cover portion to each other. The hinge portion has a pivot axis extending in a direction orthogonal to an axial line of the barrel. The base portion is provided with a locking portion. The cover portion is provided with a first locked portion locked to the locking portion and a second locked portion locked to the injection needle. The cover portion is constructed to be pivotable between a first position at which the pointed end of the needle tube is exposed as the cover portion is arranged on a side of a rear end portion of the barrel relative to the pivot axis of the hinge portion along a direction of the axial line of the barrel and the cover portion is held to the base portion as the locking portion locks the first locked portion and a second position at which the cover portion covers the pointed end of the needle tube as the cover portion is arranged on a side of the pointed end of the needle tube relative to the pivot axis of the hinge portion along the direction of the axial line of the barrel and the cover portion is held to the injection needle as the injection needle locks the second locked portion. The cover portion is located as being tilted such that the cover portion comes closer to the barrel from a side of a base end which is a side where the hinge portion is located toward a tip end which is a side where the hinge portion is not located while the cover portion is arranged in the first position and is arranged in the second position as the cover portion pivots by an angle beyond 180° around the pivot axis of the hinge portion.

Advantageous Effects of Invention

According to the present invention, an injection needle safety instrument which has a simplified construction and does not cause interference during injection and a syringe including the same can be obtained.

DESCRIPTION OF EMBODIMENTS

Figure 1:
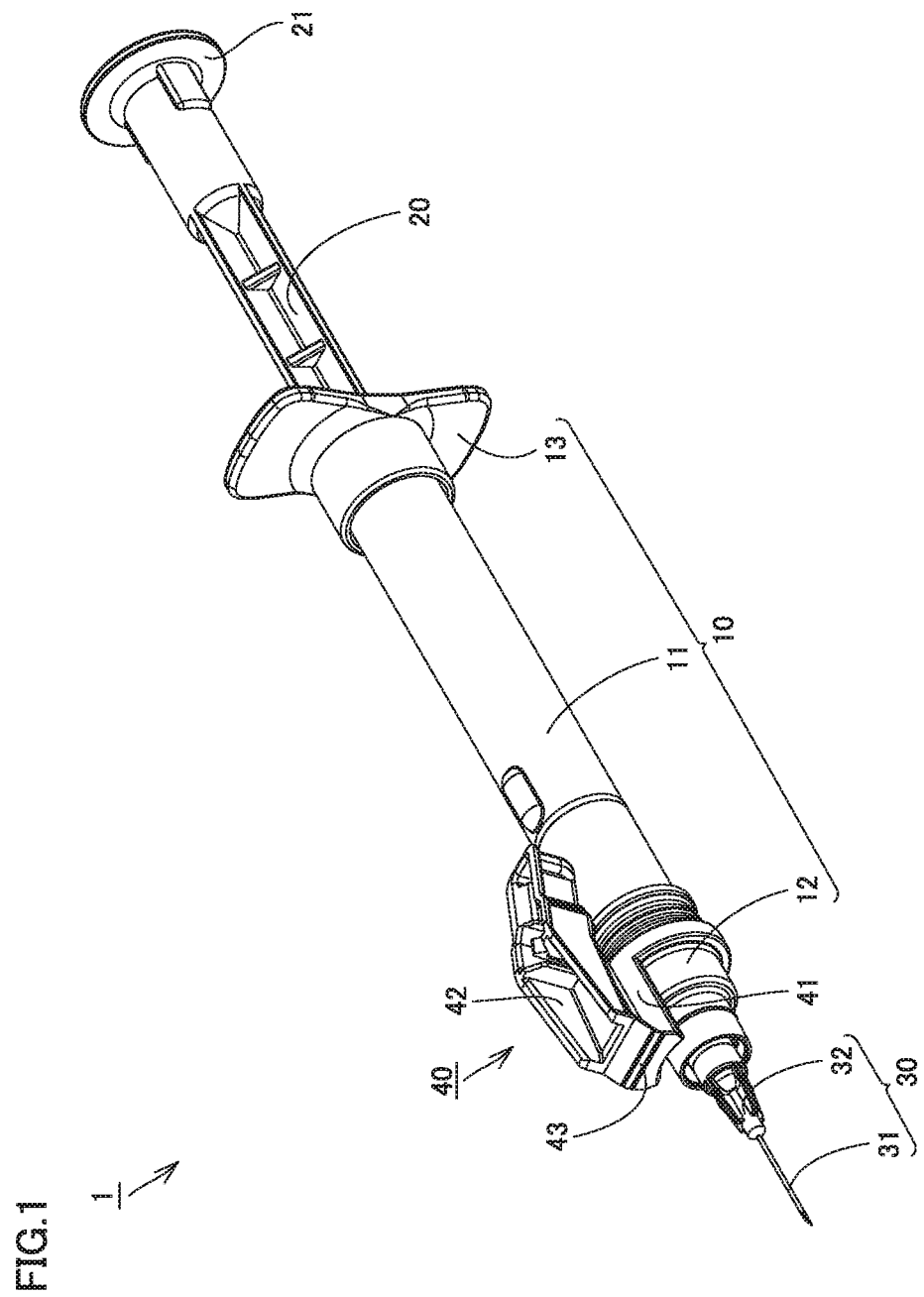
FIG. 1 is a perspective view of a syringe according to an embodiment of the present invention.

One embodiment of the present invention will be described hereinafter in detail with reference to the drawings. In the embodiment shown below, the same or common elements have the same reference characters allotted in the drawings and description thereof will not be repeated.

Figure 2:
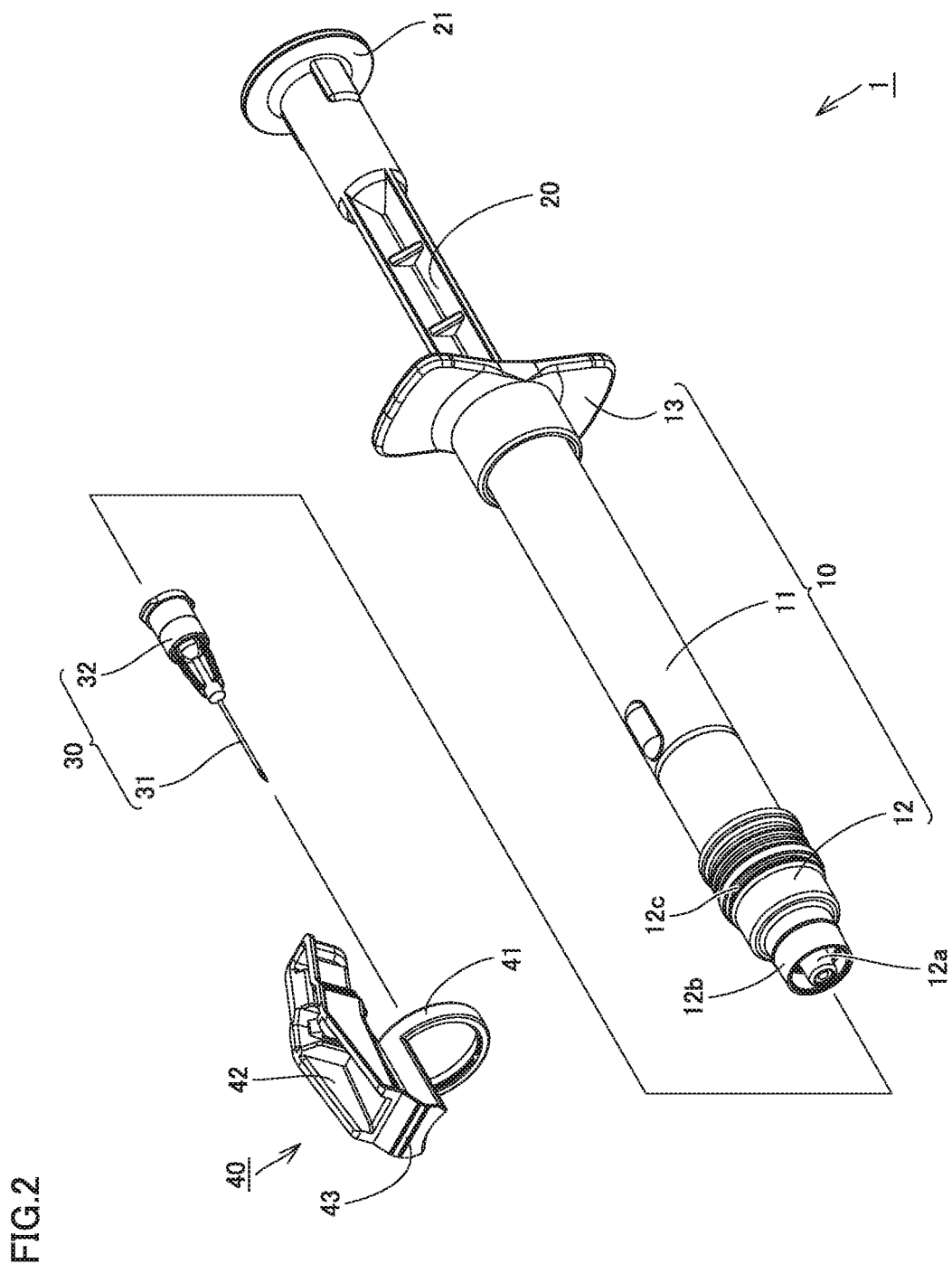
FIG. 2 is an exploded perspective view of the syringe shown in FIG. 1.
Figure 3:
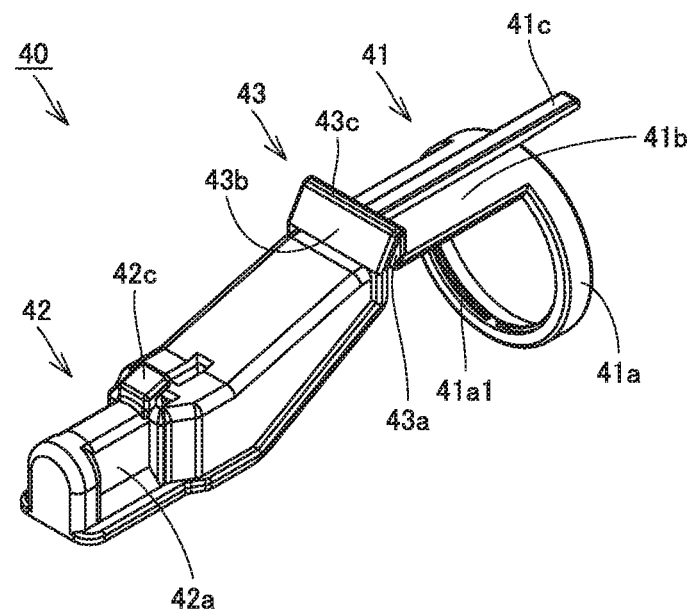
FIG. 3 is a perspective view of a developed state of an injection needle safety instrument shown in FIG. 1.
Figure 4:
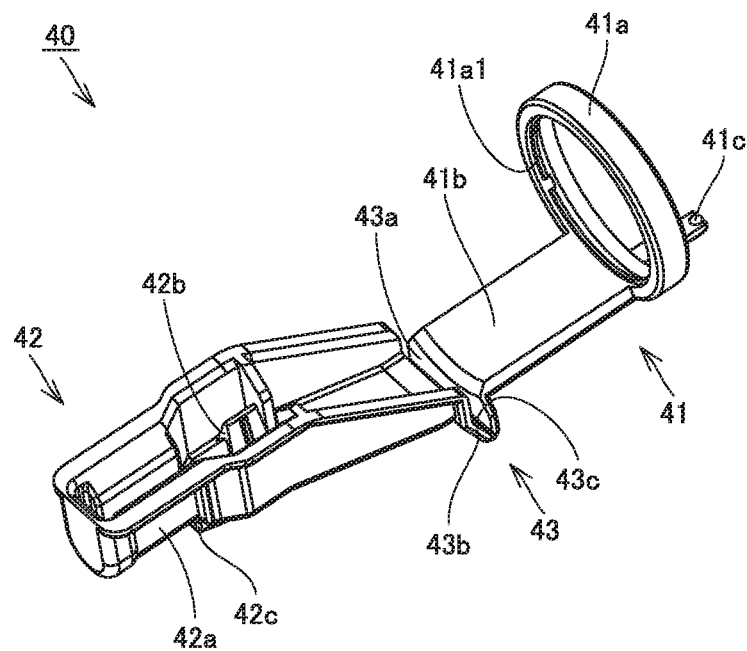
FIG. 4 is a perspective view of the developed state of the injection needle safety instrument shown in FIG. 1.
Figure 5:
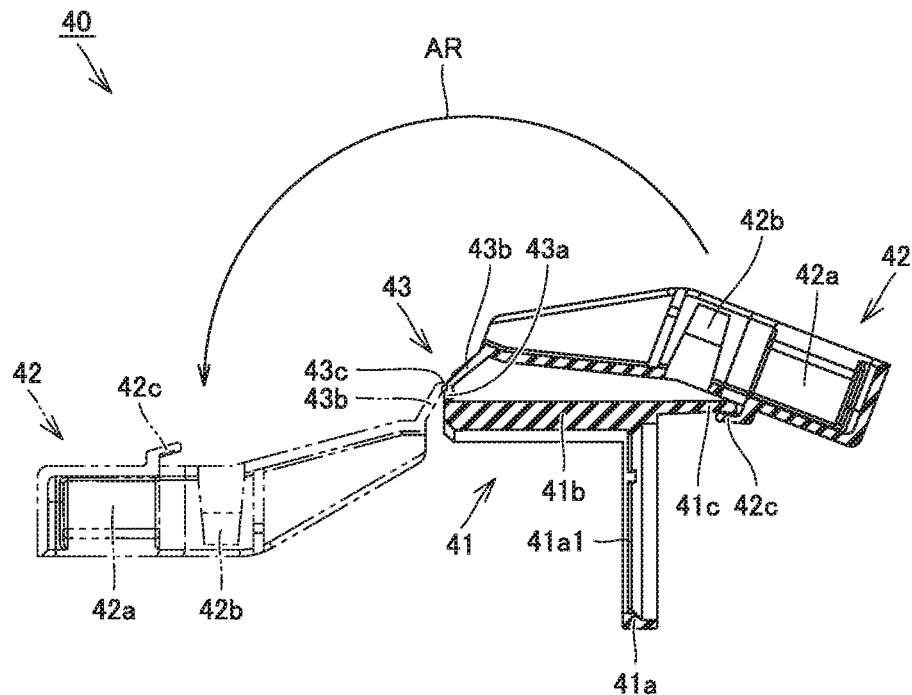
FIG. 5 is a schematic cross-sectional view showing a pivot operation of the injection needle safety instrument shown in FIG. 1.

FIG. 1 is a perspective view of a syringe according to an embodiment of the present invention and FIG. 2 is an exploded perspective view of the syringe shown in FIG. 1. FIGS. 3 and 4 are perspective views of a developed state of an injection needle safety instrument shown in FIG. 1 and FIG. 5 is a schematic cross-sectional view showing a pivot operation of the injection needle safety instrument shown in FIG. 1. A construction of a syringe in the present embodiment and a construction and a pivot operation of an injection needle safety instrument 40 included therein will initially be described with reference to FIGS. 1 to 5.

As shown in FIGS. 1 and 2, syringe 1 includes a barrel 10, a plunger 20, an injection needle 30, and injection needle safety instrument 40.

Barrel 10 includes a cylindrical body 11, an adapter 12 attached by being externally attached around a front end of cylindrical body 11, and a finger placement member 13 attached as being externally attached around a rear end of cylindrical body 11. At a front end of adapter 12, a nozzle portion 12a and a luer lock portion 12b are provided and a fitting groove 12c is provided in an outer circumferential surface of a portion of adapter 12 externally attached around cylindrical body 11.

Cylindrical body 11 is a portion mainly filled with a medicament and in a substantially cylindrical shape. Nozzle portion 12a is a portion for discharging a medicament in barrel 10 and in a substantially cylindrical shape. Luer lock portion 12b is a portion for attaching injection needle 30 to barrel 10 and in a substantially cylindrical shape. Luer lock portion 12b is located to surround nozzle portion 12a. Fitting groove 12c is a portion for attaching injection needle safety instrument 40 to barrel 10 and formed from a groove in an annular shape.

A discharge port for discharging a medicament is provided at a tip end of nozzle portion 12a, and it is connected to a needle tube 31 of injection needle 30 while injection needle 30 is attached to a front end portion of barrel 10. A female screw for screwing a needle hub 32 provided at a rear end of injection needle 30 is provided in an inner circumferential surface of luer lock portion 12b, and injection needle 30 is attached to the front end portion of barrel 10 by screwing needle hub 32 into the female screw. Finger placement member 13 is a portion where fingers are placed for pushing plunger 20 into barrel 10 at the time of injection.

Plunger 20 includes a rod in a form of a bar, a flange portion 21 provided at a rear end of the rod, and a not-shown gasket attached to a front end of the rod.

Plunger 20 serves to discharge a medicament from the discharge port described above to the outside by being pushed into barrel 10. The gasket attached to the front end of the rod is a portion for liquid tight sealing of barrel 10 and for pushing the medicament toward the discharge port by sliding through the inside of cylindrical body 11 when the rod is pushed. Flange portion 21 is a portion where a finger is placed in order to push plunger 20 into barrel 10 at the time of injection.

As described above, injection needle 30 includes needle tube 31 and needle hub 32. Needle tube 31 is formed from a thin tube made of a metal and has a sharply pointed end. Needle tube 31 is pierced through the skin of a patient so as to subcutaneously administer a medicament discharged from nozzle portion 12a of barrel 10 to the patient. Needle hub 32 is formed from a member made of a resin and has a protrusion provided at a rear end, which is screwed into the female screw of luer lock portion 12b described above. Needle hub 32 is a portion for fixing injection needle 30 to barrel 10 and needle tube 31 is fixed to needle hub 32, for example, with an adhesive.

Injection needle safety instrument 40 serves to prevent inadvertent sticking of the pointed end of needle tube 31 of injection needle 30 into a finger or the like after syringe 1 is used, and is used as being assembled to barrel 10. As shown in FIGS. 1 to 4, injection needle safety instrument 40 includes a base portion 41, a cover portion 42, and a hinge portion 43, and is made of an injection molded product consisting of a single member which is made, for example, of a resin. For example, a polyethylene resin, a polypropylene resin, a polystyrene resin, a polycarbonate resin, a transparent ABS resin, and an AS resin can suitably be employed as a material for injection needle safety instrument 40.

As shown in FIGS. 3 and 4, base portion 41 includes a fixed portion 41a in an annular shape, an extension portion 41b provided to extend from a prescribed position in a circumferential direction of fixed portion 41a toward the front end, and a locking portion 41c provided to protrude from the prescribed position of fixed portion 41a toward the rear end. A fitting protrusion 41a1 constructed to be fitted into fitting groove 12c provided in the outer circumferential surface of adapter 12 of barrel 10 described above is provided on an inner circumferential surface of fixed portion 41a. Fixed portion 41a is a portion for assembling injection needle safety instrument 40 to barrel 10, and it is fixed to barrel 10 as fitting protrusion 41a1 is fitted into fitting groove 12c as a result of external attachment around adapter 12 of barrel 10 at the time of assembly.

Cover portion 42 includes an accommodation portion 42a in a shape of a box having one opening surface, a first locked portion 42c provided to protrude from a prescribed position on a side of an outer bottom surface of cover portion 42, and a second locked portion 42b provided to protrude from a prescribed position on a side of an inner bottom surface of cover portion 42. Accommodation portion 42a is in a shape allowing coverage of a pointed end of needle tube 31 of injection needle 30 by accommodating the pointed end of needle tube 31. First locked portion 42c is in a shape of a hook in an L shape in a side view, which can be locked by locking portion 41c provided in base portion 41 described above, and second locked portion 42b is in a shape of a hook (that is, a shape of a hook which can be caught by needle tube 31) in a V shape in a front view, which can be locked by needle tube 31 of injection needle 30.

Hinge portion 43 is a portion which pivotably couples base portion 41 and cover portion 42 to each other, and includes a first arm portion 43a continuing to a front end of extension portion 41b of base portion 41 described above, a second arm portion 43b continuing to a base end of accommodation portion 42a of cover portion 42 described above, and a small-thickness portion 43c continuing to first arm portion 43a and second arm portion 43b. Small-thickness portion 43c serves as a pivot axis of hinge portion 43, as the small-thickness portion is formed to be smaller in thickness than first arm portion 43a and second arm portion 43b. First arm portion 43a is erected from the front end of extension portion 41b of base portion 41 in a direction orthogonal to a direction of extension of extension portion 41b.

As shown in FIG. 5, injection needle safety instrument 40 configured as above is constructed to be able to perform a pivot operation along a direction shown with an arrow AR in the figure with small-thickness portion 43c provided in hinge portion 43 being defined as the pivot axis, as base portion 41 and cover portion 42 are coupled to each other by hinge portion 43. FIG. 5 shows with a solid line, cover portion 42 in a state that first locked portion 42c provided in cover portion 42 is locked by locking portion 41c provided in base portion 41, and shows with a chain line, cover portion 42 in a state that locking of first locked portion 42c by locking portion 41c is released.

Figure 6:
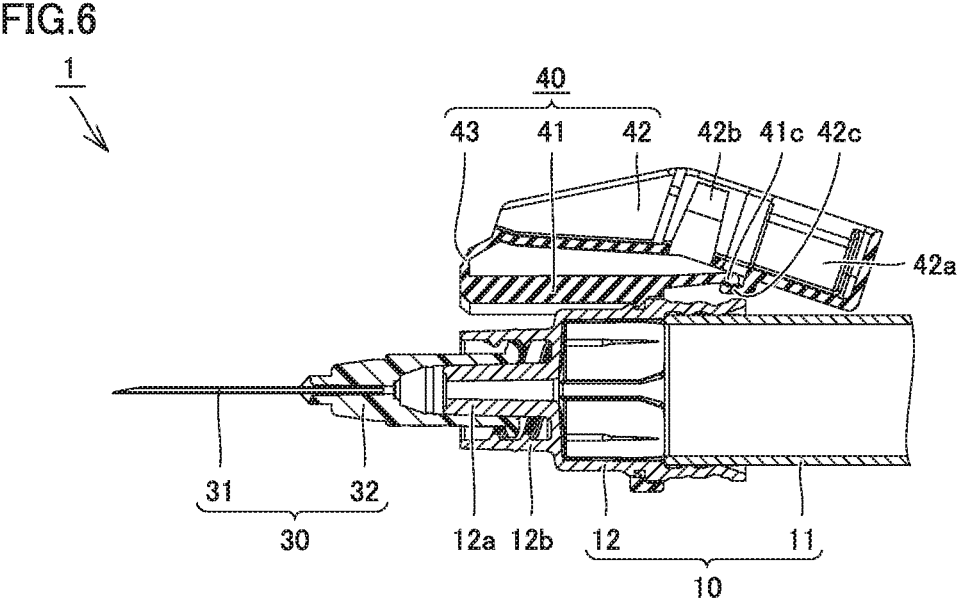
FIG. 6 is a schematic cross-sectional view showing a state that a cover portion is held by a base portion (a cover portion is in a first position), for illustrating a method of using the syringe shown in FIG. 1.
Figure 7:
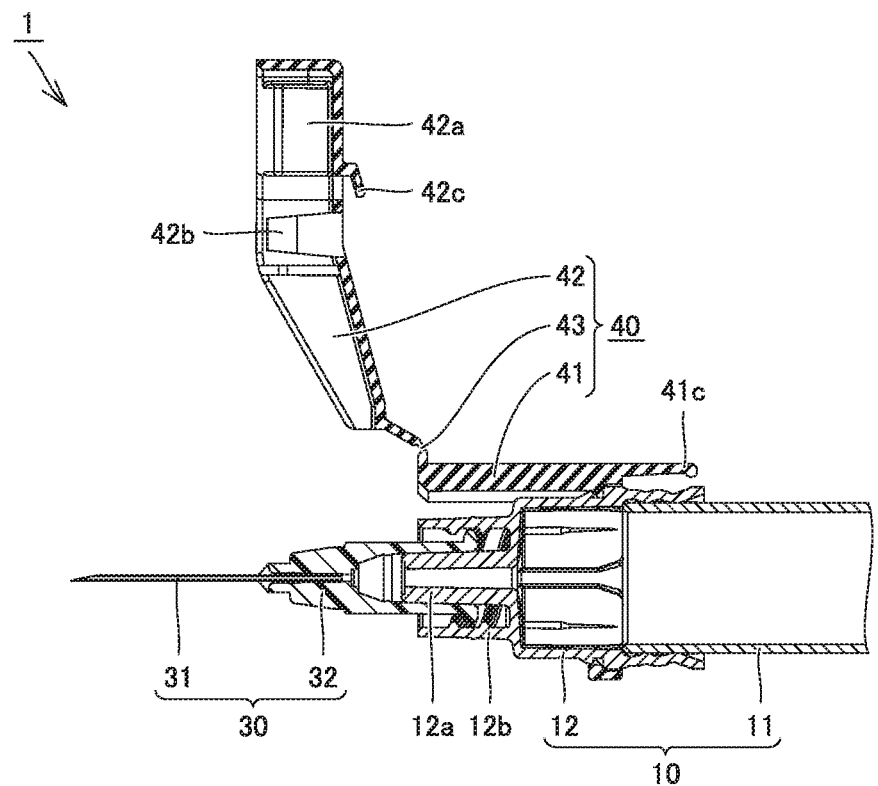
FIG. 7 is a schematic cross-sectional view showing a state that holding of the cover portion by the base portion is released, for illustrating the method of using the syringe shown in FIG. 1.
Figure 8:
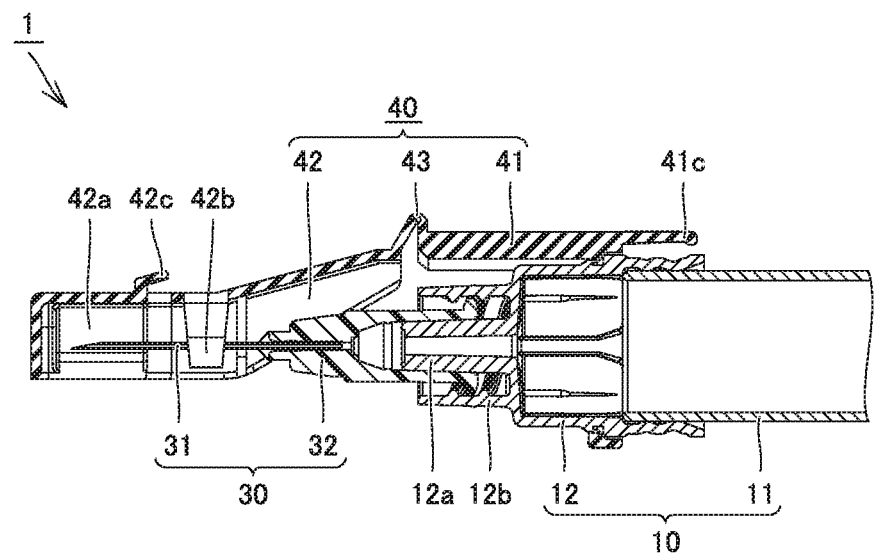
FIG. 8 is a schematic cross-sectional view showing a state that the cover portion is held by an injection needle (the cover portion is in a second position), for illustrating the method of using the syringe shown in FIG. 1.
Figure 9:
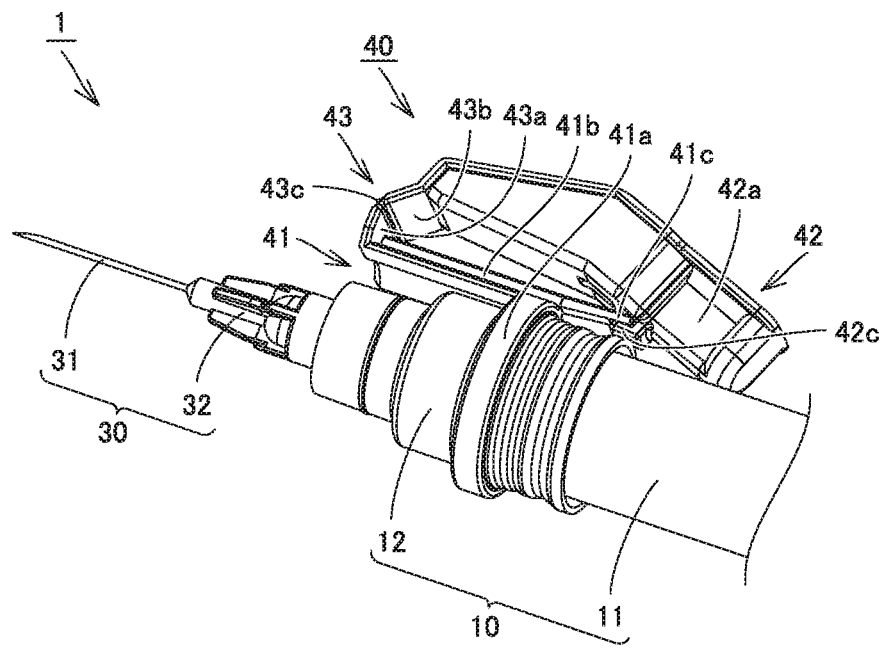
FIG. 9 is an enlarged perspective view of a main portion of the syringe in the state shown in FIG. 6.
Figure 10:
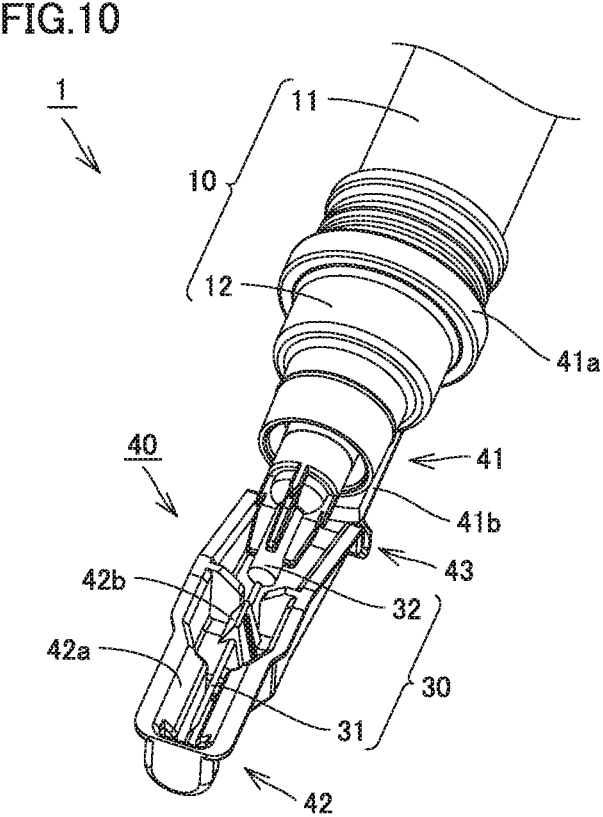
FIG. 10 is an enlarged perspective view of the main portion of the syringe in the state shown in FIG. 8.

FIGS. 6 to 8 are diagrams for illustrating a method of using the syringe shown in FIG. 1. FIG. 6 is a schematic cross-sectional view showing a state that the cover portion is held by the base portion (the cover portion is in a first position), FIG. 7 is a schematic cross-sectional view showing a state that holding of the cover portion to the base portion is released, and FIG. 8 is a schematic cross-sectional view showing a state that the cover portion is held by the injection needle (the cover portion is in a second position). FIG. 9 is an enlarged perspective view of a main portion of the syringe in the state shown in FIG. 6 and FIG. 10 is an enlarged perspective view of the main portion of the syringe in the state shown in FIG. 8. A method of using syringe 1 in the present embodiment and various states of injection needle safety instrument 40 in the method of use will now be described with reference to FIGS. 6 to 10.

As described above, injection needle safety instrument 40 is used as being assembled to barrel 10, and in particular, it is assumed to be assembled in advance to barrel 10 prior to injection. As shown in FIGS. 6 to 10, while injection needle safety instrument 40 is assembled to barrel 10, small-thickness portion 43c provided in hinge portion 43 of injection needle safety instrument 40 is arranged to extend in a direction orthogonal to the axial line of barrel 10. Thus, cover portion 42 of injection needle safety instrument 40 can pivot around the pivot axis of hinge portion 43 which extends in the direction orthogonal to the axial line of barrel 10 and can move in a longitudinal direction of barrel 10.

During injection, injection needle safety instrument 40 is in a state shown in FIGS. 6 and 9 (cover portion 42 is in the first position). Specifically, the first position corresponds to such a position that cover portion 42 is held by base portion 41 as locking portion 41c of base portion 41 locks first locked portion 42c of cover portion 42. While cover portion 42 is arranged in the first position, cover portion 42 is arranged on a side of the rear end portion of barrel 10 relative to the pivot axis of hinge portion 43 along the direction of the axial line of barrel 10, and therefore, the pointed end of needle tube 31 is not covered with accommodation portion 42a of cover portion 42 but is exposed.

In such a state, injection needle safety instrument 40 is in a folded shape without being developed, and cover portion 42 is arranged on an outer side of extension portion 41b of base portion 41. As cover portion 42 is arranged on the outer side of extension portion 41b of base portion 41, the cover portion may cut off the field of view of a doctor or the like who handles syringe 1 at the time of injection. Syringe 1 and injection needle safety instrument 40 in the present embodiment, however, are devised to avoid cut-off of the field of view as much as possible and they do not cause interference even during injection. Therefore, a doctor or the like can reliably visually recognize the pointed end of needle tube 31 during injection, and handleability during injection is not impaired even while injection needle safety instrument 40 is assembled to barrel 10. Details of this aspect will be described later.

After injection is completed, as shown in FIG. 7, the rear end of cover portion 42 is lifted in a direction away from base portion 41, so that locking of first locked portion 42c by locking portion 41c is released and accordingly holding of cover portion 42 to base portion 41 is also canceled. Since locking portion 41c and first locked portion 42c are both elastically deformable, first locked portion 42c goes beyond locking portion 41c easily with small force as a result of elastic deformation thereof, and locking can be released with a simplified operation. After locking is released, cover portion 42 can freely pivot around the pivot axis of hinge portion 43.

Then, cover portion 42 is further pivoted forward such that front and rear surfaces of cover portion 42 are reversed. Thus, injection needle safety instrument 40 is set to the state shown in FIGS. 8 and 10 (the state that cover portion 42 is in the second position). Specifically, the second position corresponds to such a position that cover portion 42 is held by injection needle 30 as second locked portion 42b of cover portion 42 is locked by needle tube 31 of injection needle 30. While cover portion 42 is arranged in the second position, cover portion 42 is arranged on the side of the pointed end of needle tube 31 relative to the pivot axis of hinge portion 43 along the direction of the axial line of barrel 10, and therefore the pointed end of needle tube 31 is covered with cover portion 42 as being accommodated in accommodation portion 42a of cover portion 42.

In such a state, injection needle safety instrument 40 is developed so that base portion 41, hinge portion 43, and cover portion 42 are arranged substantially on a straight line along the direction of the axial line of barrel 10. Since second locked portion 42b is elastically deformable, second locked portion 42b is pressed against needle tube 31 so that second locked portion 42b readily elastically deforms with small force and goes beyond needle tube 31. Thus, second locked portion 42b can be locked by needle tube 31 with a simplified operation. After second locked portion 42b is locked by needle tube 31, locking of second locked portion 42b by needle tube 31 is not released unless large external force in a specific direction which cannot be produced in normal handling is applied to cover portion 42.

Therefore, while cover portion 42 is arranged in the second position, the pointed end of needle tube 31 is covered with cover portion 42 as described above, so that inadvertent sticking of needle tube 31 of injection needle 30 into a finger or the like after syringe 1 is used can reliably be prevented.

Figure 11:
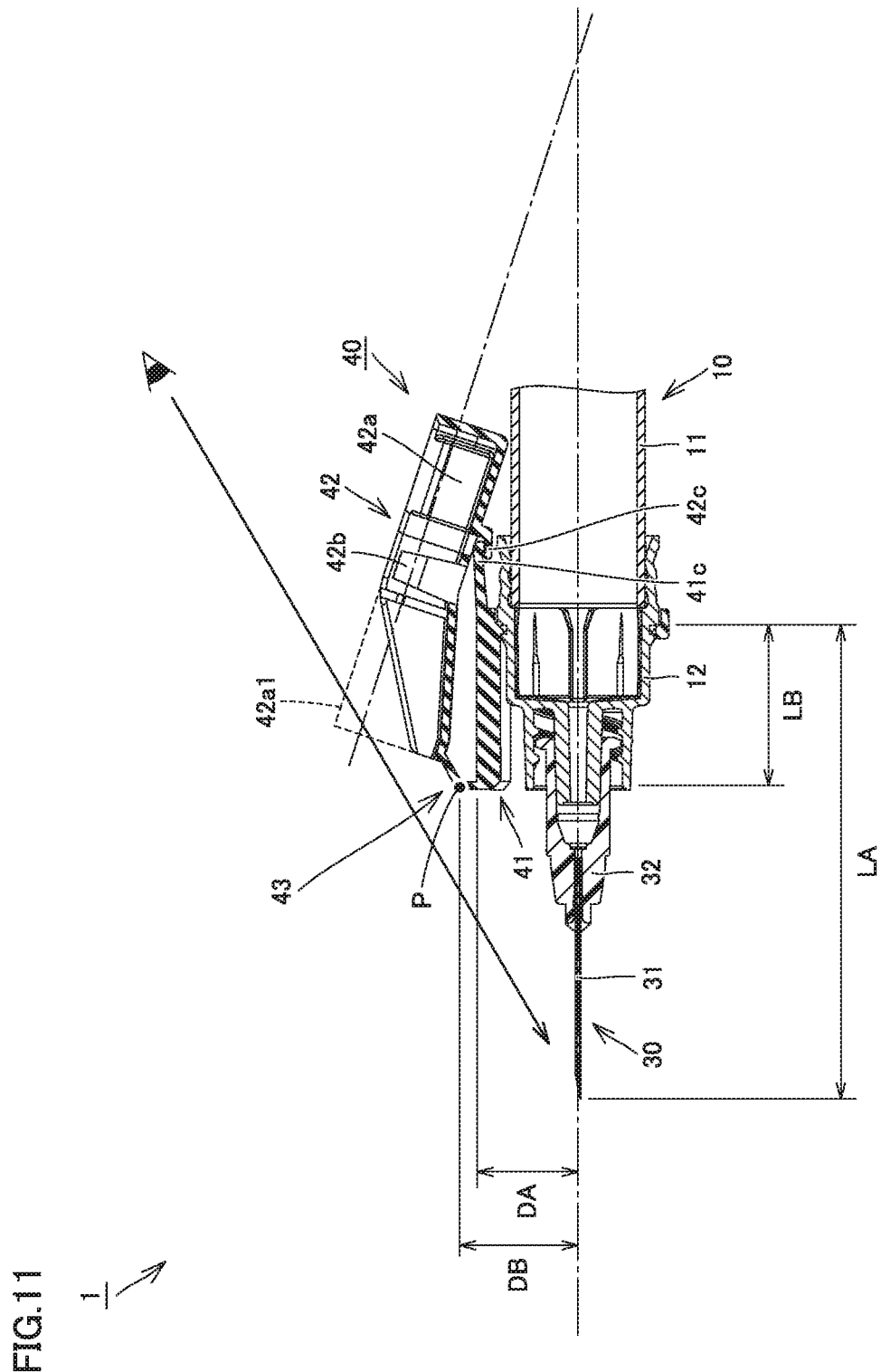
FIG. 11 is a schematic diagram for illustrating a reason why the injection needle safety instrument does not cause interference during injection in the syringe shown in FIG. 1.

FIG. 11 is a schematic diagram for illustrating a reason why the injection needle safety instrument does not cause interference during injection in syringe 1 shown in FIG. 1. A reason why injection needle safety instrument 40 does not cause interference during injection in syringe 1 in the present embodiment will then be described in detail with reference to FIG. 11.

As shown in FIG. 11, while cover portion 42 of injection needle safety instrument 40 is in the first position, cover portion 42 is arranged on the outer side of extension portion 41b of base portion 41 as described above. In syringe 1 and injection needle safety instrument 40 included therein in the present embodiment, attention is paid such that injection needle safety instrument 40 does not cause interference during injection, owing to a construction of cover portion 42 provided in injection needle safety instrument 40, in particular, owing to a construction for holding of cover portion 42 by base portion 41, a position of cover portion 42 while cover portion 42 is held by base portion 41, a position of arrangement of the pivot axis of hinge portion 43 provided in injection needle safety instrument 40, or a shape of cover portion 42.

Specifically, firstly, a construction that cover portion 42 is held by base portion 41 while cover portion 42 of injection needle safety instrument 40 is in the first position as described above is adopted. With such a construction, cover portion 42 does not move during injection, and in this sense, injection needle safety instrument 40 does not cause interference.

Secondly, while cover portion 42 of injection needle safety instrument 40 is in the first portion, cover portion 42 is in a position tilted toward barrel 10 (more specifically, a base end of cover portion 42 which is a side where hinge portion 43 is located is arranged on a relatively radially outer side of barrel 10 and the tip end (an end portion opposite to the base end) of cover portion 42 which is a side where hinge portion 43 is not located is arranged on a relatively radially inner side of barrel 10 so that cover portion 42 is tilted to come closer to barrel 10 from the base end side toward the tip end). Namely, cover portion 42 takes a position tilted toward barrel 10 while it is arranged in the first position, such that cover portion 42 arranged in the first position will be arranged in the second position described above as it pivots by an angle beyond 180° around the pivot axis (the axis shown with a point P in the figure) of hinge portion 43. With such a construction, cut-off of the field of view of a doctor or the like who handles syringe 1 during injection is avoided as much as possible, and in this sense, injection needle safety instrument 40 does not cause interference.

Thirdly, while cover portion 42 of injection needle safety instrument 40 is in the first position, fixed portion 41a of base portion 41 is arranged at a position distant from the pointed end of needle tube 31 of injection needle 30 such that the entire injection needle safety instrument 40 is arranged on the side of the rear end portion of syringe 1 as much as possible. Namely, with a long distance LA shown in the figure being ensured, cut-off of the field of view of a doctor or the like who handles syringe 1 during injection is avoided as much as possible, and in this sense, injection needle safety instrument 40 does not cause interference.

Fourthly, the pivot axis of hinge portion 43 provided in injection needle safety instrument 40 is arranged on the side of the pointed end of needle tube 31 to some extent relative to fixed portion 41a provided in base portion 41, in the direction of the axial line of barrel 10. Namely, with a considerably large distance LB shown in the figure being ensured, cover portion 42 is prevented from increasing in size, and in this sense, injection needle safety instrument 40 does not cause interference.

Fifthly, the pivot axis of hinge portion 43 provided in injection needle safety instrument 40 is arranged on the outer side relative to base portion 41 in the radial direction of barrel 10. Namely, with a distance DB shown in the figure being larger than a distance DA to some extent, while cover portion 42 of injection needle safety instrument 40 is in the first position, a state that cover portion 42 is tilted toward barrel 10 is realized and cut-off of the field of view of a doctor or the like who handles syringe 1 during injection is avoided as much as possible. In this sense, injection needle safety instrument 40 does not cause interference.

Sixthly, an outer geometry of a portion of cover portion 42 of injection needle safety instrument 40 located on a side of hinge portion 43 (that is, the portion on the side of the base end described above) is in a shape tilted to be closer to barrel 10 in a direction toward the pointed end of needle tube 31 along the direction of the axial line of barrel 10 while cover portion 42 is in the first position. With such a construction, a region 42a1 shown with a dashed line in the figure which would be produced if accommodation portion 42a of cover portion 42 may be in a shape of a common box is not present, and cut-off of the field of view of a doctor or the like who handles syringe 1 during injection is avoided as much as possible. In this sense, injection needle safety instrument 40 does not cause interference.

Seventhly, locking portion 41c provided in base portion 41 of injection needle safety instrument 40 is provided on the rear end side of barrel 10 relative to fixed portion 41a in the direction of the axial line of barrel 10. With such a construction, cover portion 42 can be held while cover portion 42 is tilted toward barrel 10, and cut-off of the field of view of a doctor or the like who handles syringe 1 during injection is avoided as much as possible. In this sense, injection needle safety instrument 40 does not cause interference.

Since injection needle safety instrument 40 has a relatively simplified construction as described above, it can be implemented by a single member without combining a plurality of members as described above, and there is no manufacturing cost pressure.

As described above, with syringe 1 and injection needle safety instrument 40 included in the same in the present embodiment, an injection needle safety instrument which has a simplified construction and does not cause interference during injection and a syringe including the same can be obtained.

Figure 12:
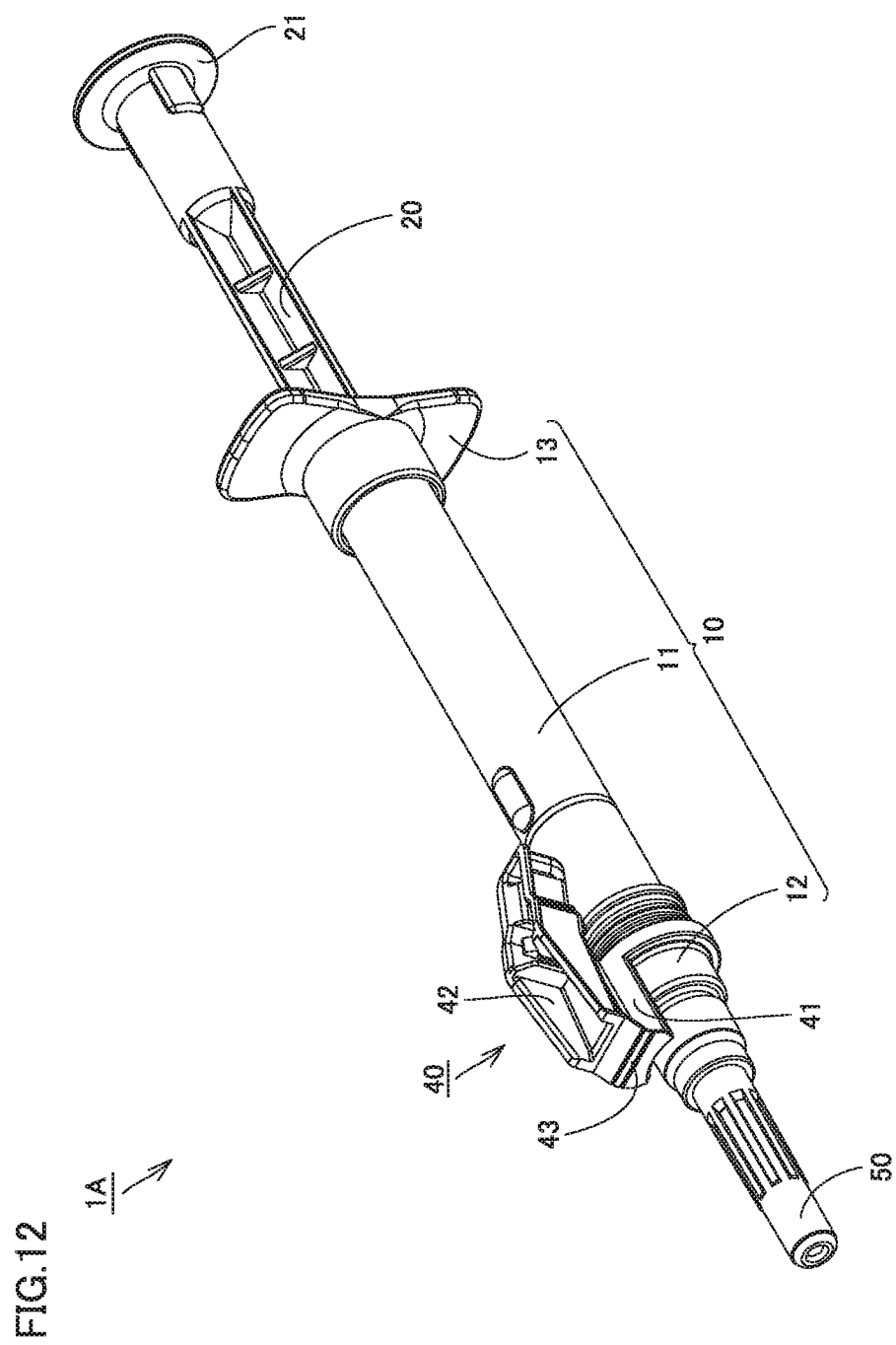
FIG. 12 is a perspective view showing a packaged state of a pre-filled syringe when the present invention is applied to the pre-filled syringe.

FIG. 12 is a perspective view showing a packaged state of a pre-filled syringe when the construction of the present invention described above is applied to the pre-filled syringe.

A pre-filled syringe 1A has barrel 10 filled with a medicament in advance, and the medicament is externally hermetically sealed by a cap 50 externally attached around luer lock portion 12b (see FIG. 2) provided in adapter 12 of barrel 10. Here, an elastic plug which closes the pointed end of needle tube 31 is provided in cap 50, and leakage of the medicament is prevented by closing of the pointed end of needle tube 31 by the elastic plug.

Thus, when the construction in the present embodiment described above is applied to pre-filled syringe 1A, pre-filled syringe 1A is packaged with injection needle safety instrument 40 in addition to cap 50 described above being assembled to barrel 10, and pre-filled syringe 1A is provided to a doctor or the like in this state.

In the embodiment of the present invention described above, description has been given with reference to an example in which a barrel is divided into a cylindrical body, an adapter, and a finger placement member and the present invention is applied to a syringe in which the barrel is constituted of combination of these components. The present invention, however, is naturally applicable also to a syringe in which a barrel consists of a single member.

In the embodiment of the present invention described above, description has been given with reference to an example in which a fitting protrusion is provided in a fixed portion of an injection needle safety instrument and a fitting groove which can be fitted to the fitting protrusion is provided in a barrel so that the injection needle safety instrument is fixed to the barrel. The injection needle safety instrument, however, may be fixed to the barrel by providing a fitting protrusion in the barrel and providing a fitting groove which can be fitted to the fitting protrusion in the fixed portion of the injection needle safety instrument.

A detailed construction of the injection needle safety instrument shown in the embodiment of the present invention described above is merely by way of example and can naturally be modified as appropriate within the scope without departing from the gist of the present invention.

The embodiment disclosed herein is thus illustrative and non-restrictive in every respect. The technical scope of the present invention is defined by the terms of the claims and is intended to include any modifications within the scope and meaning equivalent to the terms of the claims.

REFERENCE SIGNS LIST 1 syringe; 1A pre-filled syringe; 10 barrel; 11 cylindrical body; 12 adapter; 12a nozzle portion; 12b luer lock portion; 12c fitting groove; 13 finger placement member; 20 plunger; 21 flange portion; 30 injection needle; 31 needle tube; 32 needle hub; 40 injection needle safety instrument; 41 base portion; 41a fixed portion; 41a1 fitting protrusion; 41b extension portion; 41c locking portion; 42 cover portion; 42a accommodation portion; 42b second locked portion; 42c first locked portion; 43 hinge portion; 43a first arm portion; 43b second arm portion; 43c small-thickness portion; and 50 cap.

The invention claimed is:

1. A syringe comprising:
a barrel;
an injection needle attached to a front end portion of the barrel;
a plunger attached to the barrel by being inserted into the barrel from a side of a rear end portion of the barrel; and
an injection needle safety instrument assembled to the barrel,
the injection needle safety instrument including a base portion including a fixed portion fixed to the barrel, a cover portion including an accommodation portion which can cover a pointed end of a needle tube included in the injection needle by accommodating the pointed end of the needle tube, and a hinge portion which pivotably couples the base portion and the cover portion to each other,
the hinge portion having a pivot axis extending in a direction orthogonal to an axial line of the barrel,
the base portion being provided with a locking portion,
the cover portion being provided with a first locked portion locked to the locking portion of the base portion and a second locked portion locked to the injection needle,
the cover portion being constructed to be pivotable between a first position at which the pointed end of the needle tube is exposed as the cover portion is arranged on the side of the rear end portion of the barrel, the cover portion being tilted relative to the axial line of the barrel and the cover portion is held to the base portion as the locking portion locks the first locked portion and a second position at which the cover portion covers the pointed end of the needle tube as the cover portion is arranged on a side of the pointed end of the needle tube relative to the pivot axis of the hinge portion along the direction of the axial line of the barrel and the cover portion is held to the injection needle as the injection needle is locked by the second locked portion by directly engaging the second locked portion, the second locked portion being in the shape of a hook to restrict movement of the injection needle,
the cover portion is rotated about the pivot axis so that in the first position the cover portion is closer to the barrel, and when rotated about the pivot axis to the second position, the cover portion is configured to pivot by an angle greater than 180°, and
in the first and second positions, the entirety of the injection needle is parallel to the axial line of the barrel.

2. The syringe according to claim 1, wherein
while the cover portion is arranged in the first position, an entirety of the cover portion is tilted such that the accommodation portion of the cover portion is located closer to the barrel than remaining portions of the cover portion, the remaining portions including the first and second locked portions.

3. The syringe according to claim 2, wherein
the pivot axis of the hinge portion is provided on the side of the pointed end of the needle tube relative to the fixed portion in the direction of the axial line of the barrel.

4. The syringe according to claim 2, wherein
the pivot axis of the hinge portion is provided on an outer side of the base portion in a radial direction of the barrel.

5. The syringe according to claim 2, wherein
the locking portion is provided on the side of the rear end portion of the barrel relative to the fixed portion in the direction of the axial line of the barrel.

6. The syringe according to claim 2, wherein
the second locked portion is in a shape of a hook by which the needle tube can be caught.

7. The syringe according to claim 1, wherein
the pivot axis of the hinge portion is provided on the side of the pointed end of the needle tube relative to the fixed portion in the direction of the axial line of the barrel.

8. The syringe according to claim 7, wherein
the pivot axis of the hinge portion is provided on an outer side of the base portion in a radial direction of the barrel.

9. The syringe according to claim 7, wherein
the locking portion is provided on the side of the rear end portion of the barrel relative to the fixed portion in the direction of the axial line of the barrel.

10. The syringe according to claim 7, wherein
the second locked portion is in a shape of a hook by which the needle tube can be caught.

11. The syringe according to claim 1, wherein
the pivot axis of the hinge portion is provided on an outer side of the base portion in a radial direction of the barrel.

12. The syringe according to claim 11, wherein
the locking portion is provided on the side of the rear end portion of the barrel relative to the fixed portion in the direction of the axial line of the barrel.

13. The syringe according to claim 11, wherein
the second locked portion is in a shape of a hook by which the needle tube can be caught.

14. The syringe according to claim 1, wherein
the locking portion is provided on the side of the rear end portion of the barrel relative to the fixed portion in the direction of the axial line of the barrel.

15. The syringe according to claim 14, wherein
the second locked portion is in a shape of a hook by which the needle tube can be caught.

16. The syringe according to claim 1, wherein
the second locked portion is in a shape of a hook by which the needle tube can be caught.

17. The syringe according to claim 1, wherein
the injection needle safety instrument is formed from an injection molded product consisting of a single member made of a resin, and
the pivot axis of the hinge portion is formed from a small-thickness portion of which thickness is formed to be smaller than a portion around the small-thickness portion.

18. The syringe according to claim 1, wherein
the barrel includes a cylindrical body to which the plunger is attached and an adapter which is attached as being externally attached around a front end of the cylindrical body and to which the injection needle is attached, and
the injection needle safety instrument is assembled to the adapter in a portion externally attached around the cylindrical body.

19. The syringe according to claim 1, wherein the barrel is filled with a medicament as being externally hermetically sealed.

20. An injection needle safety instrument used as being assembled to a barrel of a syringe, the injection needle safety instrument comprising:
a base portion including a fixed portion fixed to the barrel of the syringe;
a cover portion including an accommodation portion which can cover a pointed end of a needle tube included in an injection needle by accommodating the pointed end of the needle tube attached to a front end portion of the syringe; and
a hinge portion which pivotably couples the base portion and the cover portion to each other,
the hinge portion having a pivot axis extending in a direction orthogonal to an axial line of the barrel,
the base portion being provided with a locking portion,
the cover portion being provided with a first locked portion locked to the locking portion of the base portion and a second locked portion locked to the injection needle,
the cover portion being constructed to be pivotable between a first position at which the pointed end of the needle tube is exposed as the cover portion is arranged on a side of a rear end portion of the barrel, the cover portion being tilted relative to the pivot axis of the hinge portion along a direction of the axial line of the barrel and the cover portion is held to the base portion as the locking portion locks the first locked portion and a second position at which the cover portion covers the pointed end of the needle tube as the cover portion is arranged on a side of the pointed end of the needle tube relative to the pivot axis of the hinge portion along the direction of the axial line of the barrel and the cover portion is held to the injection needle as the injection needle is locked by the second locked portion by directly engaging the second locked portion, the second locked portion being in the shape of a hook to restrict movement of the injection needle,
the cover portion is rotated about the pivot axis so that in the first position the cover portion is closer to the barrel, and when rotated about the pivot axis to the second position, the cover portion is configured to pivot by an angle greater than 180°, and
in the first and second positions, the entirety of the injection needle is parallel to the axial line of the barrel.

* * * * *